United States Patent [19]

Howell et al.

[11] Patent Number: 5,743,251
[45] Date of Patent: Apr. 28, 1998

[54] AEROSOL AND A METHOD AND APPARATUS FOR GENERATING AN AEROSOL

[75] Inventors: Tony M. Howell, Midlothian; William R. Sweeney, Richmond, both of Va.

[73] Assignee: Philip Morris Incorporated, New York, N.Y.

[21] Appl. No.: 648,253

[22] Filed: May 15, 1996

[51] Int. Cl.[6] .................................................. A61M 5/00
[52] U.S. Cl. .............................. 128/200.14; 128/203.25; 239/10
[58] Field of Search .......................... 131/329; 417/412, 417/474, 475, 476, 477; 250/281, 282, 288; 128/200.14, 200.18, 200.21, 203.12, 203.21, 203.25, 203.26; 239/10

[56] References Cited

U.S. PATENT DOCUMENTS

| | | |
|---|---|---|
| 3,431,393 | 3/1969 | Katsuda . |
| 3,859,398 | 1/1975 | Havstad . |
| 3,903,883 | 9/1975 | Pecina et al. . |
| 4,060,082 | 11/1977 | Lindgerg et al. ............ 417/437 |
| 4,291,838 | 9/1981 | Williams . |
| 4,303,083 | 12/1981 | Burruss, Jr. . |
| 4,575,609 | 3/1986 | Fassel et al. ............... 219/121 PY |
| 4,627,432 | 12/1986 | Newell et al. . |
| 4,730,111 | 3/1988 | Vestal et al. ............... 250/288 |
| 4,744,932 | 5/1988 | Browne . |
| 4,762,995 | 8/1988 | Browner et al. ............ 250/282 |
| 4,776,515 | 10/1988 | Michalchik . |
| 4,811,731 | 3/1989 | Newell et al. . |
| 4,819,625 | 4/1989 | Howe . |
| 4,848,374 | 7/1989 | Chard et al. . |
| 4,877,989 | 10/1989 | Drews et al. . |
| 4,911,157 | 3/1990 | Miller . |
| 4,935,624 | 6/1990 | Henion et al. ............ 250/288 |
| 5,021,802 | 6/1991 | Allred . |
| 5,044,565 | 9/1991 | Alexander . |
| 5,060,671 | 10/1991 | Counts et al. ............ 131/329 |
| 5,063,921 | 11/1991 | Howe . |
| 5,228,444 | 7/1993 | Burch . |
| 5,259,370 | 11/1993 | Howe . |
| 5,327,915 | 7/1994 | Porenski et al. . |
| 5,342,180 | 8/1994 | Daoud ..................... 417/412 |

OTHER PUBLICATIONS

"Generation of Aerosol Particles by Boiling of Suspensions", Yasuo Kousaka, et al., *Aerosol Science and Technology*, 21:236–240 (1994).

"Recommendations of the USP Advisory Panel on Aerosols on the USP General Chapters on Aerosols <601> and Uniforty of Dosage Units <905>", Peter R. Bryon, Ph.D., Chairman, *Pharmacopeial Forum*, vol. 20, No. 3, May–Jun. 1994.

*Primary Examiner*—Vincent Millin
*Assistant Examiner*—William J. Deane, Jr.
*Attorney, Agent, or Firm*—Burns, Doane, Swecker & Mathis, LLP

[57] ABSTRACT

An aerosol is formed by supplying a material in liquid form to a tube and heating the tube such that the material volatizes and expands out of an open end of the tube. The volatized material combines with ambient air such that volatized material condenses to form the aerosol. An apparatus for generating such an aerosol, and a method for generating such an aerosol, are also disclosed.

57 Claims, 4 Drawing Sheets

AEROSOL AND A METHOD AND APPARATUS FOR GENERATING AN AEROSOL

BACKGROUND AND SUMMARY OF THE INVENTION

The present invention relates generally to aerosols and, more particularly, to aerosols generated without compressed gas propellants and methods and apparatus for generating such aerosols.

Aerosols are useful in a wide variety of applications. For example, it is often desirable to treat respiratory ailments with, or deliver drugs by means of, aerosol sprays of finely divided particles of liquid and/or solid, e.g., powder, medicaments, etc., which are inhaled into a patient's lungs. Aerosols are also used for purposes such as providing desired scents to rooms, applying scents on the skin, and delivering paint and lubricant.

Various techniques are known for generating aerosols. For example, U.S. Pat. Nos. 4,811,731 and 4,627,432 both disclose devices for administering medicaments to patients in which a capsule is pierced by a pin to release a medicament in powder form. A user then inhales the released medicament through an opening in the device. While such devices may be acceptable for use in delivering medicaments in powder form, they are not suited to delivering medicaments in liquid form. The devices are also, of course, not well-suited to delivery of medicaments to persons who might have difficulty in generating a sufficient flow of air through the device to properly inhale the medicaments, such as asthma sufferers. The devices are also not suited for delivery of materials in applications other than medicament delivery.

Another well-known technique for generating an aerosol involves the use of a manually operated pump which draws liquid from a reservoir and forces it through a small nozzle opening to form a fine spray. A disadvantage of such aerosol generators, at least in medicament delivery applications, is the difficulty of properly synchronizing inhalation with pumping.

One of the more popular techniques for generating an aerosol including liquid or powder particles involves the use of a compressed propellant, often containing a chlorofluoro-carbon (CFC) or methylchloroform, to entrain a material, usually by the Venturi principle. For example, inhalers containing compressed propellants such as compressed oxygen for entraining a medicament are often operated by depressing a button to release a short charge of the compressed propellant. The propellant entrains the medicament as the propellant flows over a reservoir of the medicament so that the propellant and the medicament can be inhaled by the user. Since the medicament is propelled by the propellant, such propellant-based arrangements are well-suited for those who might have difficulty inhaling.

In propellant-based arrangements, however, a medicament may not be properly delivered to the patient's lungs when it is necessary for the user to time the depression of an actuator such as a button with inhalation. Moreover, such arrangements tend to be poorly suited for delivery of materials in large quantities. Although propellant-based aerosol generators have wide application for uses such as antiperspirant and deodorant sprays and spray paint, their use is often limited because of the well-known adverse environmental effects of CFC's and methylchloroform, which are among the most popular propellants used in aerosol generators of this type.

In drug delivery applications, it is typically desirable to provide an aerosol having average mass median particle diameters of less than 2 microns to facilitate deep lung penetration. Most known aerosol generators are incapable of generating aerosols having average mass median particle diameters less than 2 to 4 microns. It is also desirable, in certain drug delivery applications, to deliver medicaments at high flow rates, e.g., above 1 milligram per second. Most known aerosol generators suited for drug delivery are incapable of delivering such high flow rates in the 0.2 to 2.0 micron size range.

In accordance with one aspect of the present invention, an aerosol generator includes a tube having a first open end. The aerosol generator further includes means for heating the tube to a temperature sufficient to volatilize material in a liquid form in the tube such that the volatilized material expands out of the open end of the tube and mixes with ambient air to form an aerosol.

In accordance with another aspect of the present invention, a method for generating an aerosol is disclosed. According to the method, a material in liquid form is supplied to a tube having an open end. The material supplied to the tube is heated to a temperature sufficient to volatilize the supplied material such that the volatilized material expands out of the open end of the tube, the volatilized material condensing upon mixing with ambient atmospheric air to form an aerosol.

In accordance with yet another aspect of the present invention, an aerosol is provided. The aerosol is formed by supplying a material in liquid form to a tube and heating the tube such that the material volatilizes and expands out of an open end of the tube. The volatilized material combines with ambient air such that volatilized material condenses to form the aerosol.

In accordance with still another aspect of the present invention, an aerosol is provided. A first material is supplied in liquid form to a first tube and the first tube is heated such that the first material volatilizes and expands out of an open end of the first tube. A second material is supplied in liquid form to a second tube and the second tube is heated such that the second material volatilizes and expands out of an open end of the second tube. The volatilized first and second material are combined together with ambient air such that the volatilized first and second materials form first and second aerosols, respectively, the first and second aerosols being mixed to form the aerosol.

BRIEF DESCRIPTION OF THE DRAWINGS

The features and advantages of the present invention are well understood by reading the following detailed description in conjunction with the drawings in which like numerals indicate similar elements and in which.

DETAILED DESCRIPTION

Figure 1:
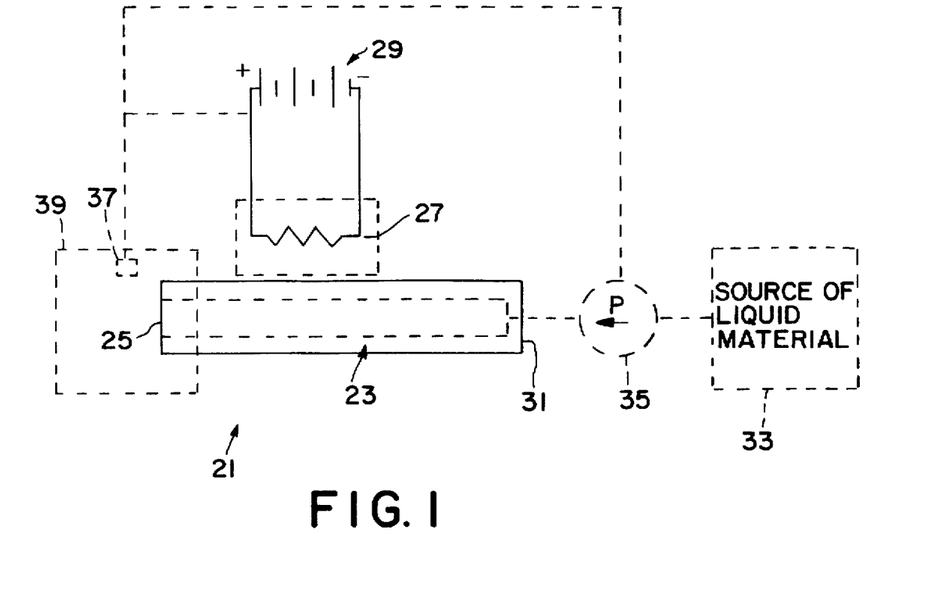
FIG. 1 is a schematic view of an aerosol generator according to a first embodiment of the present invention.

An aerosol generator 21 according to a first embodiment of the present invention is schematically shown with reference to FIG. 1. The aerosol generator 21 includes a tube 23 having an open end 25. A heater 27 is positioned adjacent to at least a portion of the tube 23, but preferably in a way that provides a heated zone around the tube that maximizes heat transfer evenly throughout the heated zone. The heater 27 is connected to a power supply 29, preferably a D.C. power supply such as a battery.

In operation, a material (not shown) in liquid form is introduced to the tube 23. The heater 27 heats the portion of the tube 23 to a sufficient temperature to volatilize the liquid material. In the case of an organic liquid material, the heater preferably heats the liquid material just to the boiling point of the liquid material, and preferably maintains the surface temperature of the tube 23 below 400° C., as most organic materials are not stable when they are exposed to temperatures above that temperature for periods of time. The volatilized material expands out of the open end 25 of the tube 23. The volatilized material mixes with ambient air outside of the tube and condenses to form particles, thereby forming an aerosol.

In a presently preferred embodiment, the tube 23 is a capillary tube or a portion thereof having an inside diameter of between 0.05 and 0.53 millimeter. A particularly preferred inside diameter of the tube is approximately 0.1 millimeter. The tube 23 is preferably a portion of a fused silica capillary column or an aluminum silicate ceramic tube, however, other substantially non-reactive materials capable of withstanding repeated heating cycles and generated pressures and having suitable heat conduction properties may also be used. If desired or necessary, an inside wall of the tube 23 may be provided with a coating for reducing the tendency of material to stick to the wall of the tube, which may result in clogging.

The tube 23 may be closed at a second end 31 and material in liquid form may be introduced into the tube 23 through the open end 25 when it is desired to form an aerosol. Thus, when the liquid material is heated by the heater 27, the volatilized material is only able to expand by exiting the tube 23 through the open end 25. However, it is preferred that the second end 31 of the tube be connected to a source 33 (shown by dotted lines in FIG. 1) of liquid material. The liquid material in the portion of the tube 23 volatilized by the heater 27 is prevented from expanding in the direction of the second end 31 of the tube, and is forced out of the open end 25 of the tube, as a result of back pressure of liquid from the source 33 of liquid material. The back pressure of the liquid is preferably between about 20 to 30 psi.

The heater 27 is preferably an electrical resistance heater. According to a preferred embodiment, the heater 27 is a heater wire having an outside diameter of 0.008 inches, a resistance of 13.1 ohms per foot, and a specific heat of 0.110 BTU/lb °F. The composition of the heater wire is 71.7% iron, 23% chromium, and 5.3% aluminum. Such a heater wire is available from Kanthal Furnace Products, Bethel, Conn.

According to another preferred embodiment, the heater 27A and 27B shown in FIGS. 2A and 2B, respectively, includes a thin platinum layer 27A' and 27B', respectively, which is deposited on the outside of a lapped ceramic capillary tube 23 serving as a substrate. In addition to the aluminum silicate ceramic tube noted above, the tube may include a ceramic such as titania, zirconia, or yttria-stabilized zirconia which does not experience oxidation at normal operating temperatures after repeated cyclings. Preferably the ceramic is alumina having an approximately 99% purity, and more preferably a 99.6% purity, available from the Accumet Engineering Corporation of Hudson, Mass.

The tube and the heater layer preferably have a roughly matching coefficient of thermal expansion to minimize thermally induced delamination. The ceramic has a determined roughness to affect the electrical resistance and to achieve adhesion of the deposited platinum layer. The platinum layer does not experience oxidation degradation or other corrosion during projected life cycles.

The thin film heater layer is deposited on the ceramic tube 23. The heater layer is preferably a thin platinum film having a thickness of, e.g., less than approximately 2 μm. The heater layer is deposited onto the tube by any suitable method such as DC magnetron sputter deposition, e.g., using an HRC magnetron sputter deposition unit, in argon at $8.0\times10^{-3}$ Torr. Alternatively, other conventional techniques such as vacuum evaporation, chemical deposition, electroplating, and chemical vapor deposition are employed to apply the heater layer to the tube.

The surface morphology of the ceramic tube substrate is important to accomplish a successful deposition of the heater layer. Preferably, the tube 23 is lapped by a conventional serrated knife. Typical lapped alumina has an unpolished surface roughness between approximately 8 and 35 microinches. The ceramic tube substrate is then polished to a surface roughness having an arithmetic average greater than approximately one microinch and, more specifically, between one and approximately 100 microinches, and most preferably between 12 and 22 microinches. If the substrate is polished to further reduce surface roughness as in conventional ceramic substrate preparation, i.e., to a surface roughness of one microinch or less, an adequate deposition interface will not be formed.

As seen in FIG. 2A, the heater layer 27A' is coupled to the power supply by means of appropriate contacts 27A" for resistive heating of the heater layer. As seen in FIG. 2B, the heater layer 27B' is coupled to the power supply by conductive posts 27B" for resistive heating of the heater layer. The contacts or posts preferably have a lower resistance than the associated heater layer to prevent or reduce heating of these connections prior to heating of the heater layer. As seen in FIG. 2A, the contacts 27A" may comprise a gold coated tungsten wire, such as a W-wire wool, commercially available from the Teknit Corporation of New Jersey, which is gold coated. Alternatively, the contacts may comprise copper leads. The contacts 27A" contact the platinum heater layer 27A' on or in the heater layer top surface or at any other location so long as an adequate electrical contact is achieved. The contacts 27A' may be electrically connected to mounds 28A' of the platinum heater layer 27A', the heater layer further having an active area 28A" for heating the tube 23 therebetween. The resistance of the heater layer 27A' is affected by the morphology of the tube 23.

As seen in FIG. 2B, electrically conductive contact posts 27B" may be used instead of the above-described contact arrangements and may be formed to improve the mechanical strength of the assembly. The contact posts are connected to the outside of the tube 23 prior to deposition of the heater layer 27B' and are connected to the power supply by means of wires. The contact posts may be comprised of any desired material having good electrical conductance such as copper or other copper alloys such as phosphur bronze or Si bronze, and are preferably copper or any alloy having at least approximately 80% copper. The posts 27B", or a bonding layer, as discussed below, provide a low electrical resistance connection for use with a desired current. If copper or a copper alloy is not employed for the posts, then preferably an intermediate copper bonding layer (not shown) is connected by any conventional technique to the end of the post to permit bonding between the post and the tube 23 without affecting the electrical path.

Figure 2A:
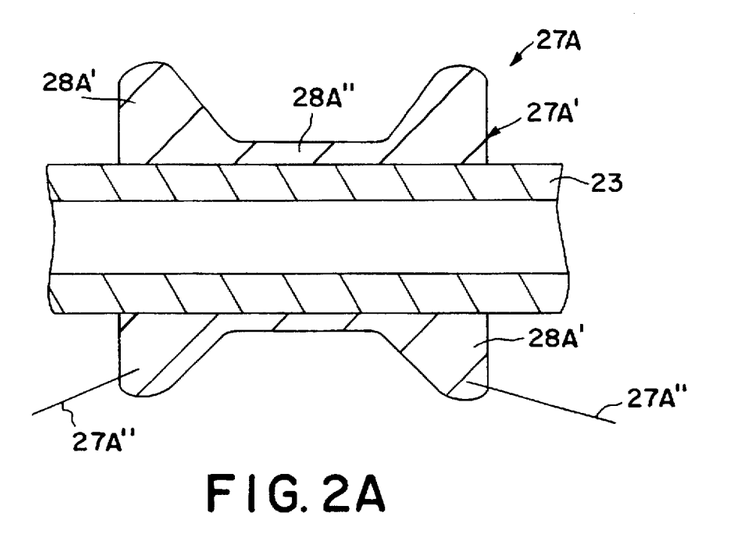
FIGS. 2A and 2B are schematic views of a portion of an aerosol generator including heaters according to embodiments of the present invention.
Figure 2B:
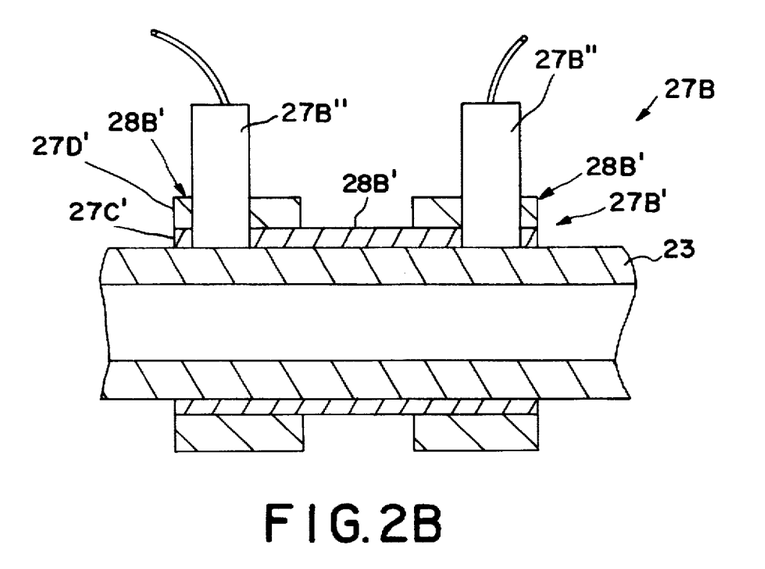

The connection of the ends of the posts 27B" to the tube 23 is preferably achieved by eutectic bonding wherein a surface of copper is oxidized, the resulting copper oxide surface is contacted with the ceramic substrate or tube, the copper-copper oxide is heated to melt the copper oxide but not the copper such that the melted copper oxide flows into grain boundaries of the ceramic, and then the copper oxide is reduced back to copper to form a strong bond. This connection can be achieved by a eutectic bonding process used by Brush Wellman Corporation of Newbury Port, Mass.

Next, the platinum heater layer 27B' is applied to the ceramic tube 23. The heater layer comprises an initial layer 27C' extending around the tube 23 and the posts 27B" and a contact layer 27D' which electrically connects the posts to the initial layer. The active heating area 28B" is defined on the portion of the heater layer 27B' which is not covered by the contact layer 27D' as a result of masking the heating area prior to applying the contact layer. Mounds or thick regions 28B' are formed by the contact layer 27D' around the posts 27B" and rise from the tube surface to function as contacts. In the embodiments illustrated in FIGS. 2A and 2B, by providing the mounds or graded regions of platinum in the heater layer, such that it is thicker at the contacts or posts than at the active portion, a stepped resistance profile results which maximizes resistance in the active portion of the heater layer.

The power supply 29 is sized to provide sufficient power for the heating element 27 that heats the portion of the tube 23. The power supply 29 is preferably replaceable and rechargeable and may include devices such as a capacitor or, more preferably, a battery. For portable applications, the power supply is, in a presently preferred embodiment, a replaceable, rechargeable battery such as four nickel cadmium battery cells connected in series with a total, non-loaded voltage of approximately 4.8 to 5.6 volts. The characteristics required of the power supply 29 are, however, selected in view of the characteristics of other components of the aerosol generator 21, particularly the characteristics of the heater 27. One power supply that has been found to operate successfully in generating an aerosol from liquid propylene glycol is operated continuously at approximately 2.5 Volts and 0.8 Amps. The power supplied by the power supply operating at this level is close to the minimal power requirements for volatizing propylene glycol at a rate of 1.5 milligrams per second at atmospheric pressure, illustrating that the aerosol generator 23 may be operated quite efficiently.

The aerosol generator 23 may generate an aerosol intermittently, e.g., on demand, or, as discussed further below, continuously. When it is desired to generate an intermittent aerosol, the material in liquid form may be supplied to the portion of the tube 23 proximate the heater 27 each time that it is desired to generate the aerosol. Preferably, the material in liquid form flows from the source 33 of material to the portion of the tube 23 proximate the heater 27, such as by being pumped by a pump 35 (shown by dotted lines).

If desired, valves (not shown) may be provided in line between the portion of the tube 23 proximate the heater 27 to interrupt flow. Preferably, the material in liquid form is pumped by the pump 35 in metered amounts sufficient to fill the portion of the tube 23 proximate the heater 27 so that substantially only the material in that portion of the tube will be volatilized to form the aerosol, the remaining material in the line between the source 33 of material and the portion of the tube 23 preventing expansion of the volatilized material in the direction of the second end 31 of the tube.

When it is desired to generate an aerosol intermittently for drug inhalation, the aerosol generator 23 is preferably provided with a puff-actuated sensor 37 (shown by dotted lines), which preferably forms part of a mouthpiece 39 (shown by dotted lines) disposed proximate the open end 25 of the tube 23, for actuating the pump 35 and the heater 27 so that material in liquid form is supplied to the tube 23 and the material is volatilized by the heater. The puff-actuated sensor 37 is preferably of the type that is sensitive to pressure drops occurring in the mouthpiece 39 when a user draws on the mouthpiece. The aerosol generator 23 is preferably provided with circuitry such that, when a user draws on the mouthpiece 39, the pump 35 supplies material in liquid form to the tube 25 and the heater 27 is heated by the power supply and the pump 35.

A puff-actuated sensor 37 suitable for use in the aerosol generator may be in the form of a Model 163PC01D35 silicon sensor, manufactured by the MicroSwitch division of Honeywell, Inc., Freeport, Ill., or an SLP004D 0-4" $H_2O$ Basic Sensor Element, manufactured by SenSym, Inc., Milpitas, Calif. Other known flow-sensing devices, such as those using hot-wire anemometry principles, are also believed to be suited for use with the aerosol generator.

The mouthpiece 39 is disposed proximate the open end 25 of the tube 23 and facilitates complete mixing of the volatilized material with cooler ambient air such that the volatilized material condenses to form particles. For drug delivery applications, the mouthpiece 39 is preferably designed to permit passage of at least approximately 60 liters of air per minute without substantial resistance, such a flow rate being the normal tidal flow for inhalation. Of course, the mouthpiece 39, if provided, may be designed to pass more or less air, depending upon the intended application of the aerosol generator and other factors, such as consumer preferences. A preferred mouthpiece for a hand held asthma inhaler is approximately 1 inch in diameter and between 1.5 and 2 inches in length, with the open end 25 of the tube 23 centered at an end of the mouthpiece.

Figure 3:
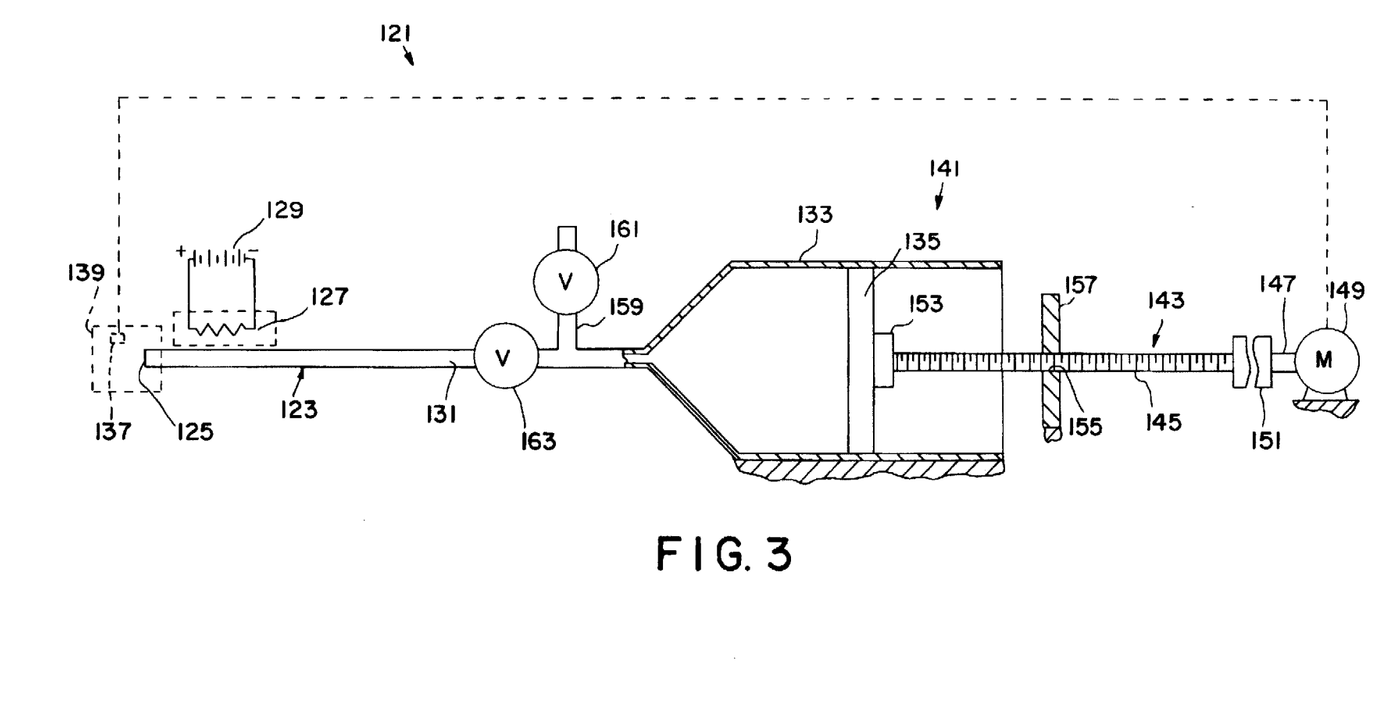
FIG. 3 is a schematic view of an aerosol generator according to a second embodiment of the present invention.

An aerosol generator 121 according to a second embodiment of the present invention is seen with reference to FIG. 3. The basic components of the aerosol generator 121 are substantially the same as the components of the aerosol generator 21 shown in FIG. 1, the aerosol generator 121 shown in FIG. 3 including a presently preferred liquid material supply assembly 135. The aerosol generator 121 includes a tube 123 having an open end 125, a heater 127 attached to a portion of the tube 123 proximate the open end, and a power supply 129 for supplying power to the heater.

A second end 131 of the tube 123 extends to a reservoir or source 133 of liquid material, such as a cylinder of a syringe, and the liquid material is delivered to the tube through the second end 131 thereof by means of a pump 135, such as a piston of the syringe. A mouthpiece 139 and puff-actuated sensor 137 (both shown by dotted lines) may be provided as well, in substantially the same manner as discussed above with regard to the aerosol generator 23.

The illustrated syringe pump 141, including the cylinder 133 and piston 135, facilitates delivery of liquid material to the tube 123 at a desired flow rate. The syringe pump 141 is preferably provided with an assembly 143 for automatically moving the piston 135 relative to the cylinder 133. The assembly 143 preferably permits incremental or continuous advancement or withdrawal of the piston 135 from the cylinder 133, as desired. If desired, of course, the piston 135 may alternatively be manually compressible.

The assembly 143 preferably includes a rod 145, at least a portion of which is externally threaded. Preferably, the rod 145 is attached at one end to a shaft 147 of a reversible motor 149, preferably an electric motor, such that operation of the motor causes the rod to rotate clockwise or counterclockwise, as desired. The rod 145 is preferably attached to the shaft 147 by means of a coupling 151 that permits axial movement of the rod relative to the shaft, but not rotational movement of the rod relative to the shaft.

An end of the rod 145 is attached to the piston 135. The rod 145 is preferably attached to the piston 135 by means of a bearing assembly 153 such that rotation of the rod does not cause rotation of the piston, however, if desired, the rod may be rigidly attached to the piston. The externally threaded portion of the rod 145 extends through an internally threaded opening 155 in a member 157, which ay simply be a nut, which is fixed in position relative to the motor 149 and the cylinder 133, both of which are preferably also fixed in position.

Preferably, when the motor 149 is operated, the shaft 147 turns the rod 145 and the rod turns in the opening 155 relative to the fixed member 157. As the rod 145 turns in the opening 155, the end of the rod attached to the piston 135 is advanced or withdrawn from the cylinder 133, depending upon the thread of the rod and the opening and the direction in which the rod is turned. The coupling 151 permits the rod 145 to move axially relative to the shaft 147. Sensors (not shown) are preferably provided to ensure that the rod 145 is not moved excessively into or out of the cylinder 133. It will be appreciated that a liquid supply arrangement such as the above-described syringe pump 141 is well suited to supply liquid at a rate of 1 milligram/second or greater, as needed, and that, provided a sufficiently powerful heater 127 is provided, an aerosol may be continuously produced at a rate of 1 milligram/second or greater, which is understood to be a much greater rate of delivery of particles in sizes between 0.2 and 2 microns mass median particle diameter than is available with conventional aerosol drug delivery systems.

It will often be desirable to minimize contact of the liquid in the cylinder 133 with oxygen, such as to avoid contamination or decomposition. To this end, the aerosol generator 121 is preferably provided with an arrangement for conveniently refilling the cylinder 133 of the syringe pump 141, such as a line 159 having a valve 161 that may be opened as the piston 135 is withdrawn in the cylinder to draw liquid from another source of supply. Another valve 163 may be provided in the tube 123 to ensure that liquid flowing into the aerosol generator is charged into the cylinder and not inadvertently wasted by flowing out of the open end 125 of the tube. If desired, a three-way valve may be provided to alternatively permit flow from the cylinder 133 to the tube 123 and from the line 159 to the cylinder.

In addition, or in the alternative, the cylinder 133 and piston 135 may be configured to be easily replaced when emptied, such as by providing appropriate fittings where the end of the cylinder meets the second end 131 of the tube 123 and where the rod 145 is attached to the piston. A new, preferably hermetically sealed piston 135 and cylinder 133 can be provided to replace a used piston and cylinder. Such an arrangement may be particularly desirable in applications such as hand held inhalers and the like.

The aerosol generator 121 may continuously generate an aerosol, such as by continuously operating the motor 149 and the heater 127 such that liquid material is continuously supplied to the tube 123 and the supplied liquid material is continuously volatilized. In addition, or in the alternative, the aerosol generator may intermittently generate an aerosol, such as by intermittently operating the motor 149 and the heater 127 such that a desired amount of liquid material is supplied to the tube 123 over a period of time and the heater is operated for a sufficient length of time to volatilize the supplied liquid, the motor and the heater thereafter being turned off. Intermittent operation in drug delivery applications is preferably achieved by actuation of the motor 149 and the heater 127 by the puff-actuated sensor 137 in combination with appropriate interconnecting circuitry. Alternative actuating devices, e.g., push buttons, may, of course, be used.

An aerosol generator 221 according to a third embodiment of the present invention is seen with reference to FIG. 4. The aerosol generator 221 includes two or more separate aerosol generators, which may be substantially the same as the aerosol generator described above, in combination. The parallel aerosol generator arrangement facilitates forming a combination aerosol formed by mixing together two or more separately generated aerosols. The parallel aerosol generator arrangement is particularly useful where it is desired to form an aerosol comprising two or more materials which do not mix well in liquid form.

Each aerosol generator preferably includes a tube 223' and 223", respectively, each tube having an open end 225' and 225", respectively. Heaters 227' and 227" are preferably provided for each tube 223' and 223", respectively, although, in some applications, it may be convenient or possible to provide a single heater for heating both tubes. The heaters are powered by power supplies 229' and 229", respectively. If desired, a single power supply may be used to power both heaters.

Each tube 223' and 223" is connected, at its second end 231' and 231", respectively, to sources 233' and 233", respectively, of first and second liquid materials. The first and second liquid materials are advanced into the tubes 223' and 223" by pumps 235' and 235", respectively. The pumps 235' and 235" may pump the first and second liquids at the same or different flow rates, as desired or necessary, and may be driven by separate driving means or by a common driving means, such as by the above-described automatic moving assembly. When the first and second liquid materials in the tubes 223' and 223" are volatilized by the heaters 227' and 227", respectively, and expand out of the open ends 225' and 225" of the tubes, respectively, the volatilized first and second materials are mixed together in a mixing chamber, such as a mouthpiece 239, and mix with ambient air so that hey condense and form an aerosol. A puff-actuated sensor 237 may be used to actuate components such as the one or more power supplies and one or more motors for driving the pumps.

Where liquids are conveniently miscible, it may also be desirable to combine, e.g., two or more liquids in one or more tubes or a manifold in a location between a source 233' and 233'" of the liquids and a portion of the tube that is heated by the heater. The liquids may be supplied together to the tube 223' from the sources 233' and 233'" by separate pumps 235' and 235'", respectively, at the same or different flow rates, as desired or necessary, and the pumps may be driven by separate or common driving means. The heater 227' heats the tube 223' to a temperature sufficient to volatilize the mixed liquid materials, the volatilized mixed liquid materials expanding out of the open end 225' of the tube and condensing to form a combination aerosol. If desired, the combination aerosol formed of the pre-mixed liquids may be combined with other aerosols to form still further combination aerosols.

The characteristics of the aerosol generated by the aerosol generator according to the present invention are generally functions of various parameters of the aerosol generator and the liquid material supplied to the aerosol generator. For aerosols intended for inhalation, for example, it is desirable for the aerosol to be at approximately body temperature when inhaled and for mass median particle diameter of particles of the aerosol to be less than 2 microns, preferably between 0.2 and 2 microns, and more preferably between 0.5 and 1 micron.

It has been observed that liquid materials such as propylene glycol and glycerol can be formed into aerosols having mass median particle diameters and temperatures in the preferred ranges. While not wishing to be bound by theory, it is believed that the extremely small mass median particle diameters of the aerosol according to the present invention are achieved at least in part as a result of the rapid cooling and condensation of the volatilized material that exits the heated tube. Manipulation of parameters of the aerosol generator such as the internal diameter of the tube, heat transfer characteristics of the tube, heating capacity of the heater, and the rate at which material in liquid form is supplied to the tube are presently expected to affect aerosol temperature and mass median particle diameter. While testing on materials other than propylene glycol and glycerol to date has been limited, it is anticipated that further testing on other materials in liquid form, e.g., liquid drugs and powdered drugs dissolved or suspended in solution, e.g., solutions of propylene glycol or glycerol, including materials having physical characteristics differing from those of propylene glycol and glycerol, will yield results analogous to those of propylene glycol.

Certain components in solid, i.e., powdered, form may be mixed with desired liquid component so that the resulting solution is formed into an aerosol in the manner described above. Where the solid component is of the type that remains suspended in the particular liquid material used, the solid component is forced out of the open end of the tube with the volatilized material. The resulting aerosol consists of particles resulting from the condensation of the volatilized material and the solid component particles. Where certain types of solid component particles are, in solution, larger than the particles resulting from the condensation of the volatilized material, the resulting aerosol may include particles of the solid component that are larger than the particles resulting from the condensation of the volatilized material.

Figure 4:
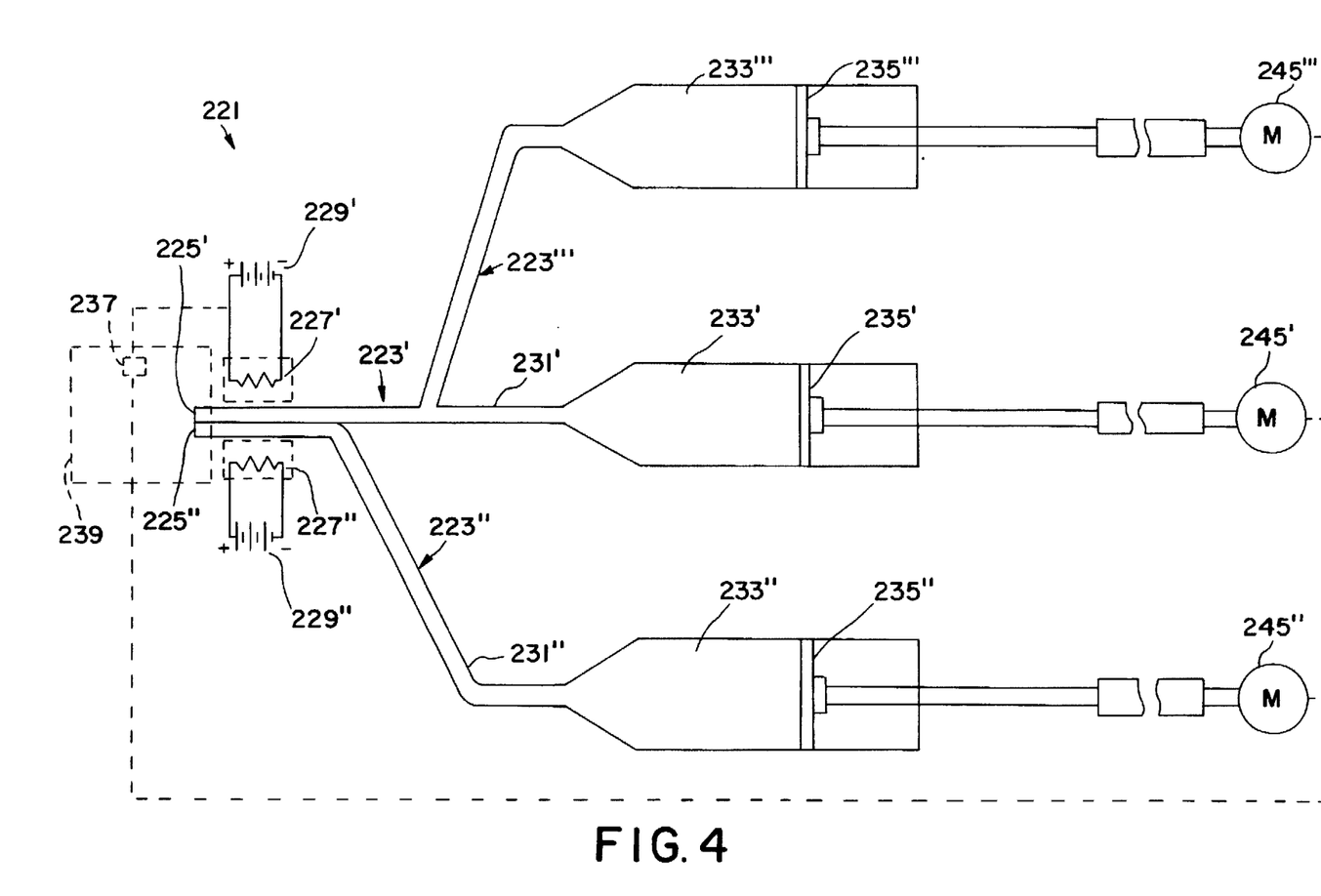
FIG. 4 is a schematic view of an aerosol generator according to a third embodiment of the present invention.

A method for generating an aerosol according to the present invention will now be described with reference to the aerosol generator 221 shown in FIG. 4. A material in liquid form is supplied to the tube 223' having the open end 225'. The material supplied to the tube 223' is heated by the heater 227' to a temperature sufficient to volatilize the supplied material such that the volatilized material expands out of the open end 225' of the tube. The volatilized material condenses upon mixing with ambient atmospheric air, preferably in a mouthpiece 239, to form the aerosol.

Material may be intermittently supplied to the tube 223' and the supplied material may be intermittently heated to a temperature sufficient to volatilize the material by intermittently operating the heater 227' and the pump 235'. The puff-actuated sensor 237 may be used to intermittently actuate the heater 227' and the motor 245' for driving the pump 235' when a user draws on the mouthpiece 239. The pump 235' and the heater 227' may, however, be manually actuated, e.g., by a push button arrangement and appropriate circuitry. It will further be appreciated that the pump 235' and the heater 227' may be automatically actuated. For example, the pump 235' and the heater 227' may be actuated by a timer for periodic introduction of a drug in aerosol form to a patient on a respirator. The pump 235' and the heater 227' may, further, be continuously operated to continuously form an aerosol.

If desired, a second material in liquid form may be supplied from a source of the second material 233" to a second tube 223" having an open end 225". The second material supplied to the second tube 223" is heated by a separate heater 227" to a temperature sufficient to volatilize the supplied second material such that the volatilized second material expands out of the open end 225" of the second tube. If desired, the second material supplied to the second tube 223" may be heated by the same heater 227' that heats the first tube 223'. The volatilized first material and the volatilized second material that expand out of the open ends of the tube 223' and the second tube 223", respectively, are mixed together with ambient air such that the volatilized material and the volatilized second material form first and second aerosols, respectively. The first and second aerosols are mixed with each other to form a combination aerosol including the first and second aerosols. The mixing of the first and second volatilized materials with each other and with air to form the first and second aerosols and the combination aerosol preferably takes place in a mixing chamber which, in the case of aerosol generators for drug delivery, is preferably the mouthpiece 239.

In addition to or as an alternative to mixing the first and second aerosols as described above, if desired, a third material in liquid form may be supplied from a third source 233'" of liquid material to, e.g., the tube 223' together with the first material. The first material and the second material supplied to the tube 223' are heated by the heater 227' to a temperature sufficient to volatilize the first material and the second material such that the volatized first material and second material expand out of the open end 225' of the tube together.

Solid particles may be suspended in solution in the material in liquid form supplied from the source of material. When the material in liquid form including the suspended solid particles is heated by a heater, the solid particles are forced out of the open end of the tube as the volatilized material expands such that the aerosol includes condensed particles of the material and the solid particles. The solid particles, when suspended in solution, may be of a larger average diameter than particles of the material in aerosol form. Moreover, the solid particles, when they form a part of the aerosol, may be of a larger average diameter than particles of the material in aerosol form.

It will be appreciated that embodiments of the aerosol generator according to the present invention may be fairly large, such as a table-top mounted item, but may also be miniaturized to be hand held. The ability of the aerosol generator to be miniaturized is, in large part, due to the highly efficient heat transfer between the heater and the tube which facilitates battery operation of the aerosol generator with low power requirements.

For purposes of performing runs in connection with our aerosol generator, a laboratory unit was designed which contained the basic elements of the generator, but which was modular in construction so that the various components could be exchanged after running. During most of the runs it was possible to measure the surface temperature of the heater and the power applied. Aerosol mass median particle diameter was obtained using a cascade impactor in accordance with the methods specified in the Recommendations of the USP Advisory Panel on Aerosols on the General Chapters on Aerosols (601) and Uniformity of Dosage Units (905), *Pharmacopeial Forum.* Vol. 20, No. 3, pp. 7477 et. seq. (May–June 1994) and mass was measured gravimetrically as collected from the impactor.

In the Examples that follow, the aerosol generator included a section of fused silica capillary tubing, more particularly, phenyl-methyl deactivated capillary guard columns for gas chromatography, available from Restek Corporation, Bellefonte, Pa., which was carefully wrapped with a 0.008" OD, 13.1 ohms per foot, heating wire, marked K-AF, available from Kanthal Corp., Bethel, Conn., to form a 1.0 to 1.5 cm long heating zone. The wire was wrapped in a fashion that produced close, tight coils to insure good heat transfer to the tube. The point of the needle of a Model 750N 500 microliter syringe, available from Hamilton Company, Reno, Nev., was cut off and smoothed to yield a blunt end. The blunt end was connected to the capillary tube using common gas chromatography capillary column hardware. Either a ceramic or quartz tube (¼" ID), slotted for electrical connections, was placed around the heated zone for insulation.

The syringe body was loaded onto a Model 44 programmable syringe pump, available from Harvard Apparatus, Inc., South Natick, Mass. The end of the capillary tubing was centered and supported inside a mouthpiece that was machined for mating to the induction port that connected to a MOUDI model 100 cascade impactor, available from MSP Corporation, Minneapolis, Minn., as per the Recommendations of the USP Advisory Panel on Aerosols on the General Chapters on Aerosols (601) and Uniformity of Dosage Units (905), *Pharmacopeial Forum.* Vol. 20, No. 3, pp. 7477 et. seq. (May–June 1994).

Electrical connections were made to the heater wire leads from a model TP3433A triple output DC power source, manufactured by Power Designs, Inc., Westbury, N.Y., and a microminiature open junction thermocouple was gently placed against one of the heater coils about midway along the heated zone. Computer controlled solid state switches were used to precisely time the start of the syringe pump with the power to the heater wire. Power and temperature measurements were recorded every tenth of a second by a computer using LAB TECH NOTEBOOK software, available from Laboratory Technologies, Wilmington, Mass., and a DT2801 I/O board, available from Data Translation, Inc., Marlboro, Mass.

The cascade impactor was operated according to the manufacturer's specifications. All runs were conducted with an impactor air flow rate of 30 liters per minute and a total aerosol production of less than 100 mg. We found that a loading of 30 to 40 mg in the impactor gave fairly consistent results and less problems with plugging.

During the following runs, it was desired to apply sufficient power to the heater to heat the fluid in the capillary tube so that it reached its boiling point and vaporized it before it exited the tube. It was further desired to heat the vapor sufficiently to prevent condensation at the exit of the capillary tube. There are losses to the surrounding environment which should be considered in the power equation, and these losses are device dependent.

In practice, with the particular aerosol generating device used during the following runs, the device was operated several times to determine the power required to hold the heater at a specific temperature in order to determine the losses to the surroundings. To obtain a rough estimate of total power required, the theoretical amount of energy required for heating and vaporization was added to the loss power. Several trial runs were performed to visually observe the vapor exiting the tube and the aerosol formation. When no condensation at the capillary was seen, then the power was adjusted down until condensation occurred, after which enough additional power was added so that the device was operated just above the condensation threshold. It is contemplated that numerous refinements will be made to commercial aerosol generating devices and to the manner in which power levels are set in such devices.

The following examples reflect various runs performed with the aerosol generator set up and operated as described above:

EXAMPLE I

A 0.1 mm ID capillary column was wrapped with 11.5 cm of heater wire to form a 1.0 cm heating zone with 2.0 cm of wire left at each end as leads for electrical connections. Approximately 0.5 cm of column was left unwrapped on one end to allow for connection to the syringe needle and about 0.3 cm was left unwrapped on the opposite end. Propylene glycol was drawn into the syringe and the unit was assembled as described above. The syringe pump was set to deliver 30 mg of fluid at a rate of 1.5075 mg/sec. Table 1 shows the results of the runs.

TABLE I

| Run no. | Feed Flow (mg/sec) | Power (W) | Temp. (Celsius) | % Mass Recovery | Mass Median Particle Diameter (microns) |
|---|---|---|---|---|---|
| 1 | 1.5075 | 2.92 | 289 | 66.1 | 0.56 |
| 2 | 1.5075 | 2.96 | 212 | 66.3 | 0.60 |
| 3 | 1.5075 | 3.03 | 278 | 60.0 | 0.62 |
| 4 | 1.5075 | 2.96 | 223 | 68.4 | 0.56 |
| 6 | 1.5075 | 4.21 | 384 | 40.7 | 0.91 |
| 7 | 1.5075 | 4.24 | 385 | 51.4 | 0.99 |
| 8 | 1.5075 | 4.37 | 393 | 49.6 | 1.10 |
| 9 | 1.5075 | 4.37 | 389 | 56.0 | 0.86 |
| 10 | 1.5075 | 3.60 | 355 | 58.9 | 0.61 |
| 11 | 1.5075 | 3.71 | 358 | 63.7 | 0.62 |
| 12 | 1.5075 | 3.49 | 348 | 47.5 | 0.67 |
| 13 | 1.5075 | 2.28 | 260 | 20.8 | 1.42 |
| 16 | 1.5075 | 2.27 | 248 | 22.7 | 1.22 |
| 22 | 1.5075 | 3.17 | 318 | 44.3 | 0.55 |

Figure 5:
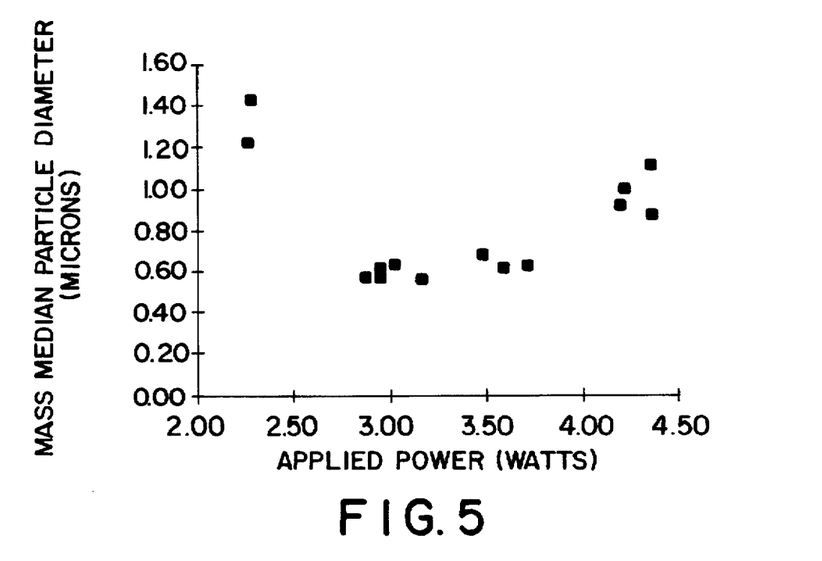
FIG. 5 is a graph of the effects of power applied in the aerosol generator on the mass median particle diameter of an aerosol generated thereby, according to the present invention.

In run numbers 6, 7, 8 and 9 the heater was somewhat overpowered and in tests 13 and 16 the heater was slightly underpowered. FIG. 5 shows the effects of the power on the mass median particle diameter of the aerosol.

EXAMPLE II

This series of runs was identical to EXAMPLE I except that the mass median particle diameter was measured against changes in feed rate. The results are shown in Table II.

TABLE II

| Run no. | Feed Flow (mg/sec) | Power (W) | Temp. (Celsius) | % Mass Recovery | Mass Median Particle Diameter (microns) |
|---|---|---|---|---|---|
| 17 | 3.0151 | 4.74 | 335 | 25.4 | 0.57 |
| 18 | 3.0151 | 5.12 | 395 | 29.6 | 0.53 |
| 19 | 3.0151 | 5.05 | 427 | 16.8 | 0.90 |
| 20 | .7546 | 1.92 | 271 | 35.5 | 1.11 |
| 21 | .7546 | 2.07 | 292 | 40.4 | 0.82 |

EXAMPLE III

In EXAMPLE III, the same device configuration was used as in EXAMPLES I and II, except that glycerin was used in lieu of propylene glycol as the fluid. Note that two separate feed flow rates were employed and the results as shown in Table III indicate a smaller mass median particle diameter for glycerin than for propylene glycol.

TABLE III

| Run no. | Feed Flow (mg/sec) | Power (W) | Temp. (Celsius) | % Mass Recovery | Mass Median Particle Diameter (microns) |
|---|---|---|---|---|---|
| 23 | 1.8352 | 4.68 | 370 | 78.0 | 0.50 |
| 24 | 1.8352 | 4.56 | 347 | 69.7 | 0.60 |
| 25 | 3.6704 | 8.07 | 469 | 57.4 | 0.37 |

EXAMPLE IV

One run was performed to determine the effects of adding a higher boiling component to a lower boiling fluid. A solution of 5% wt/wt glycerin in propylene glycol was chosen as the fluid for this test. The device was the same as used for the previous examples. Test 10 was with pure propylene glycol and is shown for comparison purposes. Note the lower mass median particle diameter for the mixture.

TABLE IV

| Run no. | Feed Flow (mg/sec) | Power (W) | Temp. (Celsius) | % Mass Recovery | Mass Median Particle Diameter (microns) |
|---|---|---|---|---|---|
| 26 (5% Glycerin) | 1.5075 | 3.64 | 318 | 48.1 | 0.35 |
| 10 (PG) | 1.5075 | 3.60 | 355 | 58.9 | 0.61 |

EXAMPLE V

A new configuration was constructed for this series of runs. The capillary tube segment was a 0.05 mm ID tube in place of the 0.1 mm ID tube. Only propylene glycol was used as the fluid. All other procedures remained the same as in the previous EXAMPLES. Table V shows the entire series of runs conducted with the 0.05 mm ID tube. As in the case of the 0.1 mm tube, the fluid feed rates were varied in an effort to optimize the mass median particle diameter to the smallest diameter.

TABLE V

| Run no. | Feed Flow (mg/sec) | Power (W) | Temp. (Celsius) | % Mass Recovery | Mass Median Particle Diameter (microns) |
|---|---|---|---|---|---|
| 27 | 1.5075 | 2.75 | 419 | 34.8 | .56 |
| 28 | 1.5075 | 2.09 | 351 | 22.9 | 1.98 |
| 30 | 0.7529 | 2.43 | 387 | 48.9 | 0.64 |
| 31 | 0.7529 | 2.40 | 393 | 34.2 | 0.67 |
| 32 | 0.7529 | 2.11 | 355 | 28.0 | 0.63 |
| 33 | 0.3782 | 1.24 | 282 | 25.9 | 2.63 |
| 34 | 03.782 | 1.70 | 380 | 60.2 | 1.58 |
| 35 | 0.3782 | 2.13 | 462 | 25.9 | 1.74 |
| 36 | 0.3782 | 2.16 | 460 | 36.7 | 1.63 |
| 37 | 0.3782 | 2.22 | 460 | 59.0 | 1.36 |
| 38 | 0.7546 | 1.93 | 309 | 30.5 | 0.90 |
| 39 | 0.7546 | 2.39 | 344 | 34.6 | 0.64 |
| 40 | 1.5075 | 3.23 | 355 | 23.8 | 1.38 |
| 41 | 1.5075 | 3.78 | 366 | 54.3 | 0.50 |
| 42 | 1.5075 | 3.79 | 362 | 57.7 | 0.49 |

EXAMPLE VI

A 0.53 mm ID tube was configured as in the device configuration section and runs 44 and 45 were made. The standard heating length of 1.25 cm did not appear to be sufficient to affect good heat transfer without excessive wall temperatures. Surface temperatures for these runs were not measured as they were outside of the 500 degrees Celsius range of the equipment that we were using. A new configuration was made with the 0.53 mm ID tube in which the heated zone was extended to 4.0 cm and runs 46 to 48 were made. In all cases an aerosol was formed but was accompanied by very large liquid drops which were ejected from the tube in long streams. Table VI shows the results.

TABLE VI

| Run no. | Feed Flow (mg/sec) | Power (W) | % Mass Recovery | Mass Median Particle Diameter (microns) |
|---|---|---|---|---|
| 44 | 7.9952 | 12.04 | 0.93 | 1.52 |
| 45 | 1.5075 | 4.22 | 24.85 | 4.24 |
| 46 | 7.9952 | 4.80 | 12.55 | 1.62 |
| 47 | 7.9952 | 6.02 | 21.95 | 1.76 |
| 48 | 7.9952 | 13.5 | 11.30 | 1.54 |

The runs conducted with our aerosol generator reveal that the configurations with the 0.05 mm ID tube and the 0.53 mm tube, EXAMPLES V AND VI, respectively, that such configurations are operable. However, from a practical standpoint, small ID tubes appear to require great pressures to move the fluid and are prone to plugging and breakage. Larger bore tubing presents heat transfer difficulties requiring high surface temperatures and/or extremely long heating zones to obtain good results.

While this invention has been illustrated and described in accordance with a preferred embodiment, it is recognized that variations and changes may be made therein without departing from the invention as set forth in the claims.

What is claimed is:

1. An aerosol generator, comprising:
   a tube having a first open end;
   means for heating the tube to a temperature sufficient to volatilize material in a liquid form in the tube such that the volatilized material expands out of the open end of the tube and mixes with ambient air to form an aerosol; and
   a mouthpiece member disposed proximate the open end of the tube.

2. The aerosol generator as set forth in claim 1, wherein the tube has an internal diameter of between approximately 0.05 and 0.53 millimeters.

3. The aerosol generator as set forth in claim 1, wherein the tube has an internal diameter of approximately 0.1 millimeter.

4. The aerosol generator as set forth in claim 1, wherein the tube is a portion of a fused silica capillary column.

5. An aerosol generator, comprising:
a tube having a first open end; and
means for heating the tube to a temperature sufficient to volatilize material in a liquid form in the tube such that the volatilized material expands out of the open end of the tube and mixes with ambient air to form an aerosol, wherein the tube is an aluminum silicate ceramic tube.

6. An aerosol generator, comprising:
a tube having a first open end; and
means for heating the tube to a temperature sufficient to volatilize material in a liquid form in the tube such that the volatilized material expands out of the open end of the tube and mixes with ambient air to form an aerosol, wherein the heating means includes a nickel-chromium heating element.

7. The aerosol generator as set forth in claim 1, wherein the heating means includes a heating element connected to a DC power supply.

8. The aerosol generator as set forth in claim 1, further comprising puff-actuating means for causing the aerosol generator to generate the aerosol when a user draws on the mouthpiece member.

9. An aerosol generator, comprising:
a tube having a first open end,
means for heating the tube to a temperature sufficient to volatilize material in a liquid form in the tube such that the volatilized material expands out of the open end of the tube and mixes with ambient air to form an aerosol; and
a mouthpiece member disposed proximate the open end of the tube,
wherein the mouthpiece member permits air flow of at least 60 liters per minute with negligible resistance.

10. The aerosol generator as set forth in claim 9, further comprising puff-actuating means for causing the aerosol generator to generate the aerosol when a user draws on the mouthpiece member.

11. The aerosol generator as set forth in claim 1, wherein a mass median particle diameter of the aerosol generated by the aerosol generator is 2 microns or less.

12. The aerosol generator as set forth in claim 1, wherein a mass median particle diameter of the aerosol generated by the aerosol generator is between 0.2 and 2 microns.

13. The aerosol generator as set forth in claim 1, wherein a mass median particle diameter of the aerosol generated by the aerosol generator is between 0.5 and 1 microns.

14. The aerosol generator as set forth in claim 1, further comprising means for supplying the material in a liquid form to the tube through a second end of the tube.

15. The aerosol generator as set forth in claim 14, wherein the material supplying means continuously supplies the material and the heating means continuously heats the material such that the aerosol generator continuously generates the aerosol.

16. The aerosol generator as set forth in claim 14, wherein the material supplying means supplies material to the tube at a rate of greater than 1 milligram/second.

17. The aerosol generator as set forth in claim 14, wherein the material supplying means includes a pump.

18. The aerosol generator as set forth in claim 17, wherein the pump includes a syringe, the syringe including a piston and a piston cylinder, and means for moving the piston in the piston cylinder.

19. The aerosol generator as set forth in claim 18, wherein the moving means includes means for moving the piston at a desired rate in the piston cylinder.

20. The aerosol generator as set forth in claim 18, wherein the moving means includes a threaded shaft attached to the piston, means for rotating the shaft, and a fixed internally threaded member through which the shaft extends, rotation of the shaft relative to the internally threaded member causing the piston to move in the piston cylinder.

21. The aerosol generator as set forth in claim 14, wherein the material supplying means includes a reservoir of material.

22. The aerosol generator as set forth in claim 20, wherein the reservoir is sealed from an outside atmosphere.

23. The aerosol generator as set forth in claim 14, further comprising a second tube having a first open end and a second end, means for supplying a second material in liquid form to the second tube through the second end of the second tube, means for heating the second tube to a temperature sufficient to volatilize the second material such that the volatilized second material expands out of the open end of the second tube, and means for mixing the volatilized material and the volatilized second material, together, with ambient air such that the volatilized material and the volatilized second material form first and second aerosols, respectively, the first and second aerosols being mixed with each other in the mixing means to form a combination aerosol including the first and second aerosols.

24. The aerosol generator as set forth in claim 23, further comprising means for supplying a third material in liquid form to the second end of the tube such that the first and third materials are supplied to the second end of the tube together, the means for heating the tube heating the tube to a temperature sufficient to volatilize both the first and the third materials such that the volatilized first and third materials expand out of the open end of the tube and mix with ambient air and with the volatilized second aerosol to form the combination aerosol.

25. The aerosol generator as set forth in claim 14, further comprising means for supplying a second material in liquid form to the second end of the tube such that the first and second materials are supplied to the second end of the tube together, the means for heating the tube heating the tube to a temperature sufficient to volatilize both the first and the second materials such that the volatilized first and second material expand out of the open end of the tube and mix with ambient air to form a combination aerosol.

26. A method for generating an aerosol, comprising the steps of:
supplying a material in liquid form to a tube having an open end; and
heating the material supplied to the tube to a temperature sufficient to volatilize the supplied material such that the volatilized material expands out of the open end of the tube, the volatilized material condensing upon mixing with ambient atmospheric air to form an aerosol.

27. The method as set forth in claim 26, wherein material is intermittently supplied to the tube and the supplied material is intermittently heated to a temperature sufficient to volatilize the material.

28. The method as set forth in claim 26, comprising the further step of actuating a material supply means for supplying material to the tube and actuating a heating means for heating the supplied material to a temperature sufficient to volatilize the material.

29. The method as set forth in claim 27, wherein the material supply means and the heating means are actuated by a puff-actuated means associated with an aerosol generating means, the puff actuating means actuating the material supply means and the heating means when a user draws on a portion of the aerosol generating means.

30. The method as set forth in claim 28, wherein the material supply means and the heating means are manually actuated.

31. The method as set forth in claim 30, wherein the material supply means and the heating means are automatically actuated.

32. The method as set forth in claim 26, wherein material is continuously supplied to the tube and the supplied material is continuously heated to a temperature sufficient to volatilize the material.

33. The method as set forth in claim 26, wherein the material is supplied at a rate greater than 1 milligram per second.

34. The method as set forth in claim 26, wherein the supplied material is volatilized at a rate of greater than 1 milligram per second.

35. The method as set forth in claim 26, wherein the aerosol has a mass median particle diameter of less than 2 microns.

36. The method as set forth in claim 26, wherein the aerosol has a mass median particle diameter of between 0.2 and 2 microns.

37. The method as set forth in claim 26, wherein the aerosol has a mass median particle diameter between 0.5 and 1 microns.

38. The method as set forth in claim 26, comprising the further steps of:

supplying a second material in liquid form to the tube together with the material;

heating the material and the second material supplied to the tube to a temperature sufficient to volatize the material and the second material such that the volatized material and second material expand out of the open end of the tube together.

39. The method as set forth in claim 26, comprising the further steps of:

supplying a second material in liquid form to a second tube having an open end;

heating the second material supplied to the second tube to a temperature sufficient to volatize the supplied second material such that the volatized second material expands out of the open end of the second tube; and mixing the volatized material and the volatized second material that expand out of the open ends of the tube and the second tube, respectively, together with ambient air such that the volatized material and the volatized second material form first and second aerosols, respectively, the first and second aerosols being mixed with each other to form a combination aerosol including the first and second aerosols.

40. A method for generating an aerosol, comprising the steps of:

supplying a material in liquid form to a tube having an open end; and heating the material supplied to the tube to a temperature sufficient to volatilize the supplied material such that the volatilized material expands out of the open end of the tube, the volatilized material condensing upon mixing with ambient atmospheric air to form an aerosol, wherein solid particles are suspended in solution in the material, the solid particles being forced out of the open end of the tube as the volatilized material expands such that the aerosol includes condensed particles of the material and the solid particles.

41. The method as set forth in claim 40, wherein the solid particles, when suspended in solution, are of a larger average diameter than particles of the material in aerosol form.

42. The method as set forth in claim 41, wherein the solid particles, when they form a part of the aerosol, are of a larger average diameter than particles of the material in aerosol form.

43. The method as set forth in claim 40, wherein the solid particles, when they form a part of the aerosol, are of a larger average diameter than particles of the material in aerosol form.

44. An aerosol formed by supplying a material in liquid form to a tube and heating the tube such that the material volatizes and expands out of an open end of the tube, the volatized material combining with ambient air such that volatized material condenses to form the aerosol.

45. The aerosol as set forth in claim 44, the aerosol having a mass median particle diameter of less than 2 microns.

46. The aerosol as set forth in claim 44, the aerosol having a mass median particle diameter of between 0.2 and 2 microns.

47. The aerosol as set forth in claim 44, the aerosol having a mass median particle diameter of between 0.2 and 2 microns.

48. The aerosol as set forth in claim 44, wherein the material includes two or more components mixed together before the material is volatized.

49. The aerosol as set forth in claim 44, wherein solid particles are suspended in solution in the material, the solid particles being forced out of the open end of the tube as the volatized material expands such that the aerosol includes condensed particles of the material and the solid particles.

50. The aerosol as set forth in claim 49, wherein the solid particles, when suspended in solution, are of a larger average diameter than particles of the material in aerosol form.

51. The method as set forth in claim 50, wherein the solid particles, when they form a part of the aerosol, are of a larger average diameter than particles of the material in aerosol form.

52. The method as set forth in claim 49, wherein the solid particles, when they form a part of the aerosol, are of a larger average diameter than particles of the material in aerosol form.

53. An aerosol formed by supplying a first material in liquid form to a first tube and heating the first tube such that the first material volatizes and expands out of an open end of the first tube, supplying a second material in liquid form to a second tube and heating the second tube such that the second material volatizes and expands out of an open end of the second tube, and combining the volatized first and second material together with ambient air such that the volatized first and second materials form first and second aerosols, respectively, the first and second aerosols being mixed to form the aerosol.

54. The aerosol as set forth in claim 53, the aerosol having a mass median particle diameter of less than 2 microns.

55. The aerosol as set forth in claim 53, the aerosol having a mass median particle diameter of between 0.2 and 2 microns.

56. The aerosol as set forth in claim 53, the aerosol having a mass median particle diameter of between 0.2 and 2 microns.

57. The aerosol as set forth in claim 53, wherein at least one of the first and second materials includes two or more components mixed together before the one of the materials is volatized.

* * * * *